(12) United States Patent
Soerens et al.

(10) Patent No.: US 7,265,192 B2
(45) Date of Patent: *Sep. 4, 2007

(54) BREATHABLE ELASTOMERIC ARTICLE

(75) Inventors: Dave A. Soerens, Neenah, WI (US); William E. Conley, Alpharetta, GA (US); Loi Vinh Huynh, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 18 days.

This patent is subject to a terminal disclaimer.

(21) Appl. No.: 10/999,805

(22) Filed: Nov. 30, 2004

(65) Prior Publication Data

US 2006/0115653 A1 Jun. 1, 2006

(51) Int. Cl.
  *A41D 19/00* (2006.01)
  *C08F 18/00* (2006.01)
  *B32B 27/32* (2006.01)
  *B05D 3/02* (2006.01)

(52) U.S. Cl. .......................... 526/320; 2/159; 526/279; 526/297; 526/332; 526/271; 526/277; 526/317.1; 428/522; 428/523.1; 428/497; 427/2.3; 427/372.2

(58) Field of Classification Search ........ 526/320, 526/271, 277, 279, 287, 332, 317.1; 428/522, 428/523.1, 497; 2/159; 427/2.3, 372.2
See application file for complete search history.

(56) References Cited

U.S. PATENT DOCUMENTS

| | | | |
|---|---|---|---|
| 3,485,787 A | 12/1969 | Haefele et al. | |
| 3,813,695 A | 6/1974 | Podell, Jr. et al. | |
| 3,830,767 A | 8/1974 | Condon | |
| 4,006,116 A | 2/1977 | Dominguez | |
| 4,039,629 A | 8/1977 | Himes et al. | |
| 4,041,103 A | 8/1977 | Davison et al. | |
| 4,386,179 A | 5/1983 | Sterling | |
| 4,481,323 A | 11/1984 | Sterling | |
| 4,499,154 A | 2/1985 | James et al. | |
| 4,511,354 A | 4/1985 | Sterling | |
| 4,548,844 A | 10/1985 | Podell et al. | |
| 4,613,640 A | 9/1986 | Deisler et al. | |
| 4,777,073 A | 10/1988 | Sheth | |
| 5,112,900 A | 5/1992 | Buddenhagen et al. | |

(Continued)

FOREIGN PATENT DOCUMENTS

EP    0815880 A2    1/1998

(Continued)

OTHER PUBLICATIONS

Test No. IST-70.4-99 entitled "*Standard Test Method For Water Vapor Transmission Rate Through Nonwoven and Plastic Film Using A Guard Film And Vapor Pressure Sensor*"from INDA (Association of the Nonwoven Fabrics Industry).

*Primary Examiner*—Kevin R. Kruer
(74) *Attorney, Agent, or Firm*—Dorrity & Manning, P.A.

(57) ABSTRACT

The present invention is directed to breathable elastomeric articles. The articles of the present invention may allow the transmission of water vapor while still providing an effective barrier to virus, bacteria, contaminants, bodily fluids, and the like. In general, a breathability additive may be incorporated into the polymer matrix of one or more layers of the elastomeric article to improve the breathability of the layer.

36 Claims, 2 Drawing Sheets

U.S. PATENT DOCUMENTS

| | | |
|---|---|---|
| 5,407,715 A | 4/1995 | Buddenhagen et al. |
| 5,534,350 A | 7/1996 | Liou |
| 5,670,263 A | 9/1997 | Gazeley |
| 5,695,868 A | 12/1997 | McCormack |
| 5,792,531 A | 8/1998 | Littleton et al. |
| 5,855,999 A | 1/1999 | McCormack |
| 5,884,639 A | 3/1999 | Chen |
| 5,900,452 A | 5/1999 | Plamthottam |
| 5,993,972 A | 11/1999 | Reich et al. |
| 6,015,764 A | 1/2000 | McCormack et al. |
| 6,075,179 A | 6/2000 | McCormack et al. |
| 6,172,177 B1 | 1/2001 | Wang et al. |
| 6,261,674 B1 | 7/2001 | Branham et al. |
| 6,288,159 B1 | 9/2001 | Plamthottam |
| 6,306,514 B1 | 10/2001 | Weikel et al. |
| 6,348,258 B1 | 2/2002 | Topolkaraev et al. |
| 6,737,491 B2 | 5/2004 | Soerens et al. |
| 6,772,443 B2 * | 8/2004 | Soerens et al. ............... 2/161.6 |
| 6,849,685 B2 | 2/2005 | Soerens et al. |
| 6,887,961 B2 * | 5/2005 | Soerens et al. ............. 526/320 |
| 2004/0036196 A1 | 2/2004 | Conley |
| 2004/0121158 A1 | 6/2004 | Shannon et al. |
| 2004/0255362 A1 | 12/2004 | Soerens et al. |

FOREIGN PATENT DOCUMENTS

| | | |
|---|---|---|
| EP | 0815880 A3 | 1/1998 |
| EP | 0931633 A2 | 7/1999 |
| EP | 1264684 A1 | 12/2002 |

* cited by examiner

BREATHABLE ELASTOMERIC ARTICLE

BACKGROUND OF THE INVENTION

Articles formed of elastomeric materials have been used in many applications: surgical gloves, examining gloves, food service gloves, condoms, catheters, balloons, tubing and the like. Such articles, in addition to having good elastic properties, exhibit good strength characteristics and may be produced so as to be impermeable not only to aqueous solutions, but also to many solvents and oils. Elastomeric articles have provided an effective barrier between the wearer and the environment, successfully protecting both from cross-contamination.

Elastomeric articles are typically formed so as to be stretched somewhat during normal use. For example, some articles, especially condoms and gloves, are formed so as to be stretched during donning, in order to fit tightly against the wearer and provide good gripping and tactile characteristics during use. In addition, the articles should be impermeable to undesired substances, in order to provide a barrier between the wearer and the environment in which the articles are used. Unfortunately, these desired characteristics of elastomeric articles may create a harsh environment for the wearer's skin. For example, perspiration is a common problem for wearers, and wearing an elastomeric article over a long period of time may be uncomfortable due to the trapped perspiration in the article. In addition, the moist environment in the article due to perspiration may exacerbate skin problems, including, for example, growth of fungi and yeast as well as bacterial and viral infections of the skin.

In the past, the skin contacting surface of the elastomeric articles were treated with a powder, such as cornstarch or calcium carbonate powder to improve donning. The presence of the powders may also absorb some of the moisture and alleviate some of the problems the wearers faced. The use of a powder was only partly successful, however, as there was a limited amount of moisture the powder could absorb. Additionally, in certain applications, such as cleanroom type applications and during surgical procedures, powders may not be utilized at all.

What is needed in the art is an elastomeric article that may provide the desired characteristics of either a powdered or a powder-free article, while limiting or preventing the build-up of moisture between the wearer and the article during use. In other words, what is needed in the art is a breathable elastomeric article.

SUMMARY OF THE INVENTION

The present invention is generally directed to an elastomeric article. More specifically, the article of the present invention includes a substrate body made from at least one layer of an elastomeric material. For example, in one embodiment of the present invention, the substrate body is made from an aqueous-based polymer. The polymer can be, for example, a natural rubber latex, a nitrile polymer, a silicone polymer, a polyvinyl chloride polymer, or a polyurethane polymer.

In other embodiments, the substrate body of the elastomeric article may be made from a solvent-based polymer. The solvent-based polymer may be, for instance, a synthetic block copolymer or a polyurethane polymer. Synthetic block copolymers include styrene-ethylene butylene-styrene block copolymers, styrene-isoprene-styrene block copolymers, styrene-butadiene-styrene block copolymers, styrene-isoprene block copolymers, styrene-butadiene block copolymers, and the like.

In accordance with the present invention, the at least one layer of the substrate body further includes a breathability additive. In one embodiment, the breathability additive may be comprised of about 15% to about 99.9% by mass of monoethylenically unsaturated polymer units. Suitable monoethylenically unsaturated polymers include without limitation acrylic acid, carboxylic acid, sulphonic acid, phosphonic acid, and salts of the foregoing.

In addition, a latent crosslinker may also be present in the breathability additive in an amount of from about 0.1 to about 20% by mass of acrylate or methacrylate ester units that include an alkoxysilane functionality. Upon exposure to water, the alkoxysilane functionality forms a silanol group which condenses to form a crosslinked polymer. As one example, Dow Corning produces a commercial latent crosslinker, product Z6030, which is comprised of methacryloxypropyl trimethoxy silane.

The breathability additive also includes about 0.1 to about 75% by mass of polyolefin glycol and/or polyolefin oxide units. The polyolefin glycol and/or oxide may include an alpha-olefin having about 2 to about 4 carbon atoms, and may include about 30 to about 15,000 olefin glycol and/or oxide units per molecule. The polyolefin glycol and/or oxide may be graft polymerized with the acrylate or methacrylate ester to form a graft copolymer. The polyolefin glycol and/or oxide may be a homopolymer or a copolymer. The polyolefin glycol and/or oxide may be a block copolymer including olefin glycol or oxide units having different numbers of carbon atoms, for instance, block copolymers of ethylene oxide and propylene oxide. The polyolefin glycol and/or oxide provide the breathability additive with enhanced flexibility. Thus, the breathability additive composition has enhanced adhesion in a wet condition, absorbency, and flexibility. In the past, similar compositions were used as absorbent binders as disclosed in U.S. Pat. No. 6,737,491, U.S. Patent Publication No. 20040019169, and U.S. Patent Publication No. 20040019168, which are all incorporated herein by reference.

The breathability additive can be prepared using a template polymerization process by which the monoethylenically unsaturated polymer and acrylate or methacrylate ester are polymerized in the presence of a pre-formed template polymer, which is the polyolefin glycol and/or polyolefin oxide. The polymerization can be carried out by reacting two different monoethylenically unsaturated monomers, one of which contains an alkoxysilane functionality. The polymerization may be induced by heat, radiation, redox chemical reactions, and other techniques. Suitable radiation initiators include without limitation ultraviolet, microwave, and electron beam radiation. The initiator generates free radicals to cause copolymerization of the monomers. In one embodiment, the polymerization reaction is carried out in an organic solvent such as ethanol. The polymerization may also occur in an aqueous solution, or in a combined aqueous and organic solvent.

The polyolefin glycol and/or oxide may or may not be graft polymerized onto the acrylate or methacrylate units during the polymerization process. The resulting breathability additive may contain the polyolefin glycol and/or oxide as a separate component, or as part of the copolymer, or a combination of both.

The resulting polymer has latent moisture-induced crosslinking capability due to the alkoxysilane functionality. This polymer may be applied, in a flowable state, to a substrate or other end use application. Moisture-induced crosslinking may be accomplished through hydrolysis of the alkoxysilane and subsequent condensation upon removal of the solvent from the substrate, either by evaporation of the solvent from the substrate or using any other effective technique. Alternatively, the hydrolysis of the alkoxysilane and subsequent condensation may occur after solvent removal by exposure of the coating to moisture in ambient air.

In one embodiment, the breathability additive may be constructed to have cationic functionality. Incorporating cationic functionality into the additive may make the additive more compatible with some rubber formulations, such as with formulations containing natural rubber latex. Cationic functionality may also provide some inherent antimicrobial properties. In one embodiment, for instance, cationic functionality may be incorporated into the additive by substituting acrylate or acrylamide groups with a quaternary ammonium group.

In general, the breathability additive is incorporated into the layer of the substrate body in an amount sufficient to increase the moisture vapor transmission rate of the resulting glove and/or the Mocon moisture vapor transmission rate of the resulting glove.

In one embodiment, the breathability additive may be incorporated into the layer in an amount of between about 1 and about 30 parts per hundred by weight of the material. In other embodiments, the breathability additive may be incorporated into the layer in an amount of at least 5 parts per hundred by weight.

The layer of the substrate body that contains the breathability additive of the present invention may be, in one embodiment, the primary layer of the article. The primary layer of the article as used herein refers to the layer of the article that contributes most to the physical properties of the article and generally is the layer of the article that accounts for most of the article's weight. It should be understood, however, that instead of or in addition to the primary layer, the breathability additive of the present invention may also or only be incorporated into a donning layer or a grip layer of the article. Examples of elastomeric articles, which can benefit from the present invention, may include but are not limited to surgical gloves, examining gloves, food service gloves, condoms, catheters, balloons, tubing and the like.

The present invention is also directed to a process for producing elastomeric articles, such as gloves and condoms. The process, in one embodiment, may include the steps of first providing an aqueous emulsion containing a polymer and a breathability additive. The polymer may be any suitable aqueous-based polymer such as natural rubber latex, a nitrile polymer, or a polyurethane polymer. In an alternative embodiment, the polymer may be any suitable solvent-based polymer, such as a synthetic block copolymer.

A former is then dipped into the emulsion and withdrawn from the emulsion so as to form a film on the former. The film is dried and the resulting article is stripped from the former.

Other features and aspects of the present invention are discussed in greater detail below.

BRIEF DESCRIPTION OF THE FIGURES

The present invention will be discussed with reference to the accompanying figures in which.

DETAILED DESCRIPTION OF THE INVENTION

In general, the present invention is directed to the creation of breathable elastomeric articles. Elastomeric articles may include but are not limited to surgical gloves, examining gloves, food service gloves, condoms, catheters, balloons, tubing and the like. The breathable articles of the present invention may allow the transmission of water vapor while still providing an effective barrier to an outside environment. For instance, the articles may prevent the transmission of viruses, bacteria, contaminants, bodily fluids, and the like. The articles of the present invention, however, also may reduce the amount of moisture build-up between the article and the wearer, even when the articles are worn for extended periods of time. In order to improve the breathability characteristics of an article, the present invention is generally directed to incorporation of a breathability additive into the polymer matrix of one or more layers of the article. The breathability additive may be incorporated into a primary layer of the article, a secondary layer of the article, and/or into a coating layer of the article. The breathability additive used in accordance with the present invention may comprise the reaction product of monoethylenically unsaturated polymer units, polyolefin glycol or polyolefin oxide units, and a latent crosslinker which may be, for instance, acrylate and/or methacrylate ester units that include an alkoxysilane functionality.

Once treated with a breathability additive in accordance with the present invention, the articles become breathable. The term 'breathable' as used herein, refers to a characteristic or quality of allowing any transmission of water vapor across the axial direction of the substrate body forming the article. For example, the articles of the present invention may have a water vapor transmission rate of at least about 50 gsm/24 hours, though in certain embodiments, they may have a water vapor transmission rate lower than the above exemplary water vapor transmission rate. In one embodiment, the articles may have a water vapor transmission rate of greater than about 100 gsm/24 hours. For example, the articles may have a water vapor transmission rate of greater than about 200 gsm/24 hours. In another embodiment, the articles may have a water vapor transmission rate of greater than about 400 gsm/24 hours. For example, the articles may have a water vapor transmission rate of between about 150 and about 250 gsm/24 hours. Exemplary testing procedures for determining the moisture vapor transmission rate and the water vapor transmission rate of a breathable elastomeric article are further described herein.

Figure 1:
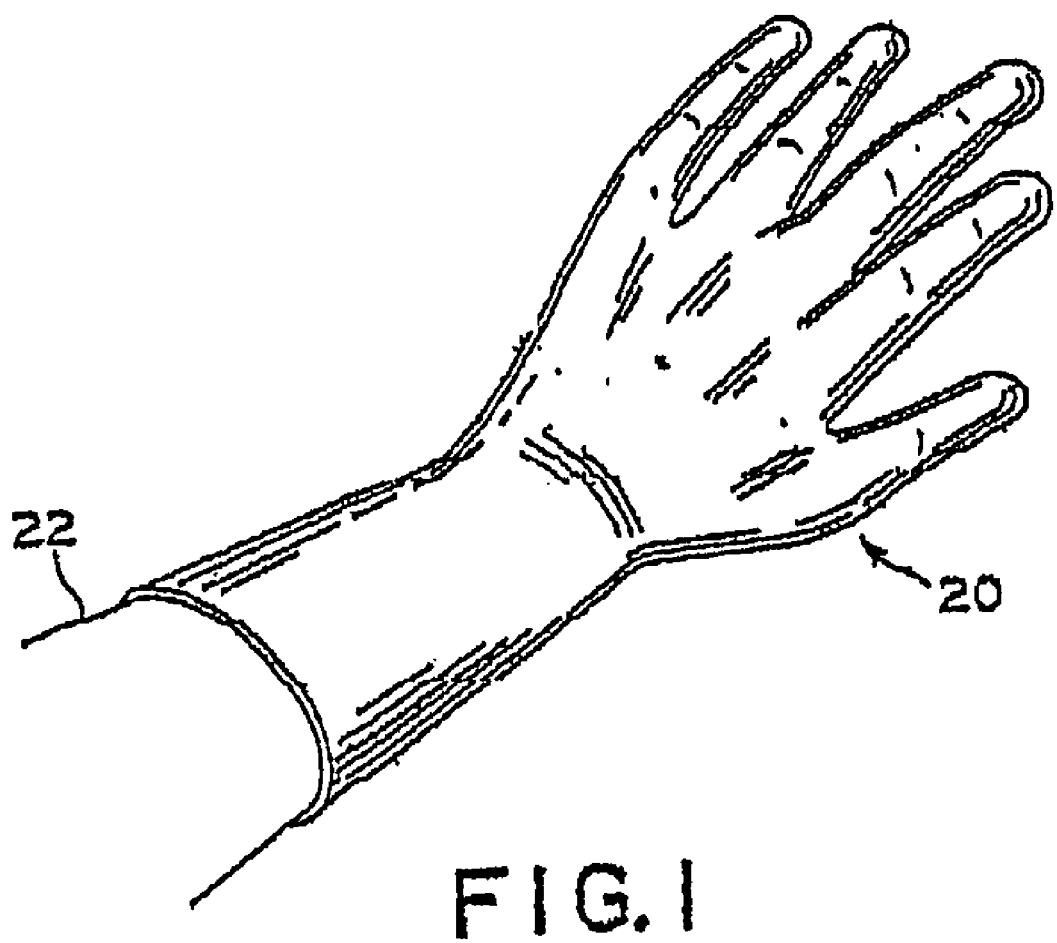
FIG. 1 is an embodiment of a glove according to the present invention.

According to an embodiment, the elastomeric article may take the form of an elastomeric glove. Referring to FIG. 1, one embodiment of an elastomeric glove 20 is illustrated that may be placed on the hand of a user 22. The glove 20 includes a substrate body having the basic shape of the glove. The substrate body may generally be formed from any of a variety of synthetic or natural polymeric elastomeric materials known in the art. In certain embodiments, the substrate body may include one or more layers of material. For instance, in some embodiments, the substrate body may include only a single breathable elastomeric layer according to the present invention. In other embodiments, however, the substrate body may include a primary elastomeric layer as well as additional layers. Additional layers may be, for example, secondary elastomeric layers in the glove interior, as well as donning layers and gripping layers.

In one embodiment of the present invention, the substrate body of the glove 20 is made from an aqueous-based polymer. As used herein, an aqueous-based polymer refers to a polymer that may be contained in an aqueous dispersion prior to formation of the glove. Examples of aqueous-based polymers that may be used in accordance with the present invention include natural rubber latex, nitrile polymers, polyvinyl chloride polymers, polyurethane polymers, silicone polymers, acrylic polymers, and the like. As used herein a nitrile polymer refers to any film-forming polymer that contains acrylonitrile.

In an alternative embodiment, the substrate body of the glove may be made from a solvent-based polymer. Solvent-based polymers include various polyurethanes and block copolymers. Particular block copolymers that may be used to construct the elastomeric article include styrene-ethylene butylene-styrene block copolymers, styrene-isoprene-styrene block copolymers, styrene-butadiene-styrene block copolymers, styrene-isoprene block copolymers, styrene-butadiene block copolymers, and the like. The solvent-based polymers may be contained in a solvent prior to formation of the glove. The solvent may be, for instance, toluene or any other suitable solvent.

In accordance with the present invention, one or more of the layers forming the substrate body of the glove may include a weight fraction of a breathability additive. The presence of the breathability additive in the layer may not interfere with the properties of the layer and may improve water vapor transmission across the layer. In one embodiment, this layer may be combined with other breathable layers to form a multi-layer, breathable glove. The other layers of a multi-layer breathable glove may be formed according to the process of the present invention, or may be otherwise breathable. For example, other layers of a multi-layer breathable glove may be discontinuous across the glove surface, such that the layer is breathable.

While not wishing to be bound by theory, it is believed that upon formation of the layer, the breathability additive may be dispersed throughout the polymer mixture, with 'islands', or areas of higher concentration of breathability additive developing as the layer is formed. The concentration of breathability additive 'islands' throughout the layer may be such that the islands may form in close proximity to one another, effectively forming a breathability additive network throughout the layer which may permit molecular diffusion of water vapor across the layer, but block the passage of liquids. In essence, a tortuous path is created from one island to the other which permits the transfer of water vapor across the layer.

In one embodiment, the breathability additive may include about 15 to about 99.9% by mass of monoethylenically unsaturated polymer units, suitably about 25 to about 90% by mass, particularly about 30-80% by mass, or about 50 to about 70% by mass. Suitable monoethylenically unsaturated polymer units include without limitation monoethylenically unsaturated carboxylic acid units and salts thereof, monoethylenically unsaturated sulphonic acid units and salts thereof, and monoethylenically unsaturated phosphonic acid units and salts thereof. Suitable monoethylenically unsaturated monomers that can be used to form the monoethylenically unsaturated polymer units include without limitation:

a) Carboxyl group-containing monomers including monoethylenically unsaturated mono or poly-carboxylic acids, such as (meth)acrylic acid (meaning acrylic acid or methacrylic acid; similar notations are used hereinafter), maleic acid, fumaric acid, crotonic acid, sorbic acid, itaconic acid, and cinnamic acid;

b) Carboxylic acid anhydride group-containing monomers, including monoethylenically unsaturated polycarboxylic acid anhydrides, such as maleic anhydride;

c) Carboxylic acid salt group-containing monomers including water-soluble salts (alkali metal salts, ammonium salts, amine salts, etc.) of monoethylenically unsaturated mono- or poly-carboxylic acids such as sodium (meth)acrylate, trimethylamine (meth)acrylate, triethanolamine (meth)acrylate, sodium maleate, methylamine maleate;

d) Sulfonic acid group-containing monomers, including aliphatic or aromatic vinyl sulfonic acids, such as vinylsulfonic acid, allyl sulfonic acid, vinyltoluenesulfonic acid, stryrene sulfonic acid, (meth)acrylic sulfonic acids, such as sulfopropyl (meth)acrylate, 2-hydroxy-3-(meth)acryloxy propyl sulfonic acid;

e) Sulfonic acid salt group-containing monomers, including alkali metal salts, ammonium salts, amine salts of sulfonic acid group containing monomers as mentioned above; and/or f) Amide group-containing monomers, including vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N, N-di-n-propylacrylamide), N-hydroxyalkyl (meth)acrylamides [such as N-methylol (meth)acrylamide, N-hydroxyethyl (meth)acrylamide], N,N-dihydroxyalkyl (meth)acrylamides, such as N,N-dihydroxyethyl (meth)acrylamide, 3-acrylamidopropyl trimethyl ammonium chloride, vinyl lactams such as N-vinylpyrrolidone.

The breathability additive also includes about 0.1 to about 20% by mass of polyacrylate ester units, such as acrylate and/or methacrylate ester units, that include an alkoxysilane functionality. The acrylate and/or methacrylate ester units are copolymerized with the monoethylenically unsaturated monomer units. In particular, the breathability additive may include about 0.5 to about 15% by mass of the acrylate and/or methacrylate ester units, for instance about 1.0 to about 10% by mass, for instance about 1.5 to about 5.5% by mass.

The alkoxysilane functionality is a functional group or moiety that reacts with water to form a silanol group. One suitable alkoxysilane group is a trialkoxy silane group having the following structure:

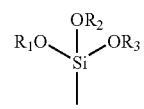

wherein $R_1$, $R_2$ and $R_3$ are alkyl groups independently having from 1 to 6 carbon atoms.

The term "monomer(s)" as used herein includes monomers, oligomers, polymers, mixtures of monomers, oligomers and/or polymers, and any other reactive chemical species which is capable of co-polymerization with monoethylenically unsaturated carboxylic, sulphonic or phosphoric acid or salts thereof. Ethylenically unsaturated monomers containing a trialkoxy silane functional group are appropriate for this invention and are desired. Suitable ethylenically unsaturated monomers include acrylates and methacrylates.

A particularly ethylenically unsaturated monomer containing a trialkoxy silane functional group is methacryloxypropyl trimethoxy silane, commercially available from Dow Corning, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, provide the desired effects and are effective monomers for copolymerization in accordance with the present invention.

In addition to monomers capable of co-polymerization that contain a trialkoxy silane functional group, it is also feasible to use a monomer capable of co-polymerization that can subsequently be reacted with a compound containing a trialkoxy silane functional group or a moiety that reacts with water to form a silanol group. Such a monomer may contain, but is not limited to, an amine or an alcohol. An amine group incorporated into the co-polymer may subsequently be reacted with, for example, but not limited to, (3-chloropropyl)trimethoxysilane. An alcohol group incorporated into the co-polymer may subsequently be reacted with, for example, but not limited to, tetramethoxysilane.

The breathability additive also includes about 0.1 to about 75% by mass polyolefin glycol and/or polyolefin oxide units, suitably about 5 to about 75% by mass, particularly about 10 to about 60% by mass, particularly about 20 to about 50% by mass, particularly about 30 to about 40% by mass. The polyolefin glycol or oxide may be a glycol or oxide of an olefin polymer having about 2 to about 4 carbon atoms. Polyethylene glycol, polyethylene oxide, polypropylene glycol and polypropylene oxide are examples of suitable polymer units. The polyolefin glycol and/or polyolefin oxide may include on average about 30 to about 15,000 glycol and/or oxide units per molecule. The weight average molecular weight of polyolefin glycol units may range from about 200 to about 8000. When polyolefin oxide units are employed, they may have a weight average molecular weight of about 100,000 to about 600,000. Polyolefin glycols and polyolefin oxides are commercially available, and are common.

In addition to the above components, the breathability additive may optionally contain various additives such as plasticizers, processing aids, rheology modifiers, antioxidants, UV light stabilizers, pigments, colorants, slip additives, antiblock agents, and the like.

To prepare the breathability additive of the invention, a pre-formed polyolefin glycol and/or oxide may be dissolved or dispersed in a reaction vessel which includes an aqueous solvent or carrier, an organic solvent or carrier such as ethanol, or a miscible combination of aqueous and organic solvent or carrier. The monomers used to form the monoethylenically unsaturated polymer units and the polyacrylate ester units are added to the solution and polymerized using a template polymerization process in which the polyolefin glycol or oxide serves as a template polymer. Before initiation, the polar groups of the monomers, for instance the acid groups of acrylic acid, are attracted to the polyolefin glycol and/or polyolefin oxide through hydrogen bonding. The steric alignment of the monomers, with the polyolefin glycol and/or oxide serving as backbone, aids in the polymerization and typically increases the chain length of the polymerizing unit. During the polymerization, radical polymerizing chains may become attached to the template polymer, resulting in grafting of polyolefin glycol and/or oxide to the copolymer being formed. However, this graft polymerization need not occur. The resulting breathability additive composition includes the polyolefin glycol and/or oxide attached to, and/or blended with, the copolymer of the monoethylenically unsaturated polymer units and the acrylate or methacrylate ester units that include the alkoxysilane functionality.

The polymerization may be initiated using a variety of methods, including without limitation thermal energy, ultraviolet light, and redox chemical reactions. A solution of the above ingredients may be added to an initiator solution at a temperature suitable for generating free radicals, for instance about 50 to about 90° C. An initiator may be prepared by dissolving an initiator in an organic or aqueous solvent. Suitable classes of initiators are organic peroxides and azo compounds, with benzoyl peroxide and azobisisobutylnitrile (ABN) as examples.

Compounds containing an O—O, S—S, or N=N bond may be used as thermal initiators. Compounds containing O—O bonds; i.e., peroxides, are commonly used as initiators for polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5-trimethylcyclohexane, 2,5-dimethyl-2,5-di(t-butylperoxy)hexane, 2,5-dimethyl-2,5-bis(t-butylperoxy)hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t-butyl peroctoate, t-butyl perbenzoate, 2,5-dimethylhexyl-2,5-di(perbenzoate) and t-butyl di(perphthalate); alkylsulfonyl peroxides; dialkyl peroxymonocarbonates; dialkyl peroxydicarbonates; diperoxyketals; ketone peroxides such as cyclohexanone peroxide and methyl ethyl ketone peroxide. Additionally, azo compounds such as 2,2'-azobisisobutyronitrile abbreviated as AIBN, 2,2'-azobis(2,4-dimethylpentanenitrile) and 1,1'-azobis(cyclohexanecarbonitrile) may be used as the initiator.

In another embodiment, the monoethylenically unsaturated polymer unit is a cationic polymer. The cationic polymer is advantageous because it provides inherent antimicrobial properties. Further, the use of a cationic polymer may make the breathability additive more compatible with various rubber formulations, such as formulations containing natural rubber latex. Suitable cationic polymers include those prepared by copolymerizing a monomer 1) selected from a) acryloyloxyethyl-trialkyl-substituted ammonium salts, b) acryloyloxypropyl-trialkyl-substituted ammonium salts, c) acrylamidoethyl-trialkyl-substituted ammonium salts, and d) acrylamidopropyl-trialkyl-substituted ammonium salts, with a monomer 2) selected from a) methacryl esters which contain an alkoxysilane group capable of moisture-induced crosslinking and b) acryl esters which contain an alkoxysilane group capable of moisture-induced crosslinking. Other monomers may also be present, for instance, an acrylic acid or acrylamide. The polymerization is conducted in the presence of a polyolefin glycol and/or polyolefin oxide as described above, suitably a polyethylene glycol. The cationic monoethylenically unsaturated monomer unit and the polyolefin glycol are present in the amounts described above.

The cationic monoethylenically unsaturated polymer may be prepared by a redox initiation process. The cationic copolymer is then coated and dried onto a substrate to form a solid that may be used as a breathability additive.

In a further embodiment, a first aqueous monomer solution including a reducing polymerization initiator is combined with a second aqueous monomer solution including an oxidizing polymerization initiator, wherein the initiators react to form a breathability additive. The first aqueous monomer solution further includes a monoethylenically unsaturated monomer and an ethylenically unsaturated monomer that contains an alkoxysilane functionality. The second aqueous monomer solution includes a monoethylenically unsaturated monomer. One or both solutions may include the polyolefin glycol and/or polyolefin oxide template polymer. Suitably, the breathability additive is formed in about 100 minutes or less, or about 60 minutes or less, desirably in about 30 minutes or less, or about 15 minutes or less, or about 10 minutes or less.

The pH of the first and/or second aqueous monomer solution is adjusted to about 4.5 to about 8, suitably about 5.5 to about 7.0. The pH of the first aqueous solution may be adjusted prior to the addition of the ethylenically unsaturated monomer. Desirably, the pH of the first aqueous monomer solution is adjusted prior to the addition of the reducing polymerization initiator. The pH of the second aqueous solution may be adjusted prior to the addition of the oxidizing polymerization initiator. Alternatively, the pH of the combined first and second aqueous monomer solutions may be adjusted to about 4.5 to about 8, suitably about 5.5 to about 7.0. If desired, the pH may be increased after polymerization is complete, by addition of a suitable basic solution. The extent of neutralization can be used to adjust the properties of the coating. Greater neutralization of the acid functional components generally enhances absorbent capacity, while greater acid functionality generally enhances adhesion.

The amounts of the polymerization ingredients added to the first and second aqueous solutions are selected so as to produce the breathability additive having the composition described above.

A surfactant may be added to the first and/or second aqueous monomer solution to disperse the ethylenically unsaturated monomer. One surfactant suitable for use in the present invention is a dioctyl sodium sulfosuccinate available under the trademark AEROSOL OT from Cytec Industries, Inc. of Paterson, N.J.

The first aqueous monomer solution further includes a reducing polymerization initiator. Suitable reducing polymerization initiators include, but are not limited to, ascorbic acid, alkali metal sulfites, alkali metal bisulfites, ammonium sulfite, ammonium bisulfite, alkali metal hydrogen sulfite, ferrous metal salts such as ferrous sulfates, sugars, aldehydes, primary and secondary alcohols, and combinations thereof. In one embodiment, the reducing polymerization initiator includes ascorbic acid.

The second aqueous monomer solution further includes an oxidizing polymerization initiator. Suitable oxidizing initiators include, but are not limited to, hydrogen peroxide, alkali metal persulfates, ammonium persulfate, alkylhydroperoxides, peresters, diacryl peroxides, silver salts, and combinations thereof. In one embodiment, the oxidizing polymerization initiator includes hydrogen peroxide.

Generally, when the first aqueous monomer solution is combined with the second aqueous monomer solution the reducing polymerization initiator reacts with the oxidizing polymerization initiator, e.g. a redox reaction, thereby initiating a polymerization reaction to form a breathability additive composition including a monoethylenically unsaturated monomer and an ethylenically unsaturated monomer that has post-application, moisture-induced crosslinking capability.

The breathability additive composition may be applied to a substrate and subsequently dried to form a cast film. Once the breathability additive composition is applied to the substrate, crosslinking can be moisture-induced by hydrolysis and condensation of alkoxysilanes. For example, crosslinking of the breathability additive composition can be induced by concentrating the breathability additive on the substrate through the removal of the water to promote condensation of silanols generated by hydrolysis of alkoxysilanes. Typically, crosslinking begins at a solution concentration of about 30 percent or greater by weight breathability additive composition. Furthermore, if the substrate material has hydroxyl group functionality on its surface, then the silanols within the breathability additive may react with the hydroxyl groups to form a covalent bond between the breathability additive and the hydroxyl-containing surface. Non-limiting examples of substrates with hydroxyl surface functionality include glass, sand and cellulose.

In another embodiment, the breathability additive may be prepared using a continuous process wherein the polymerization and/or neutralization reaction is carried out in a suitable reactor that conveys the resulting breathability additive, upon completion of the polymerization reaction, directly to an apparatus for applying the breathability additive onto the substrate. Such a continuous process may be desirable where conditions, such as high heat, may cause premature crosslinking of the breathability additive that would hinder application of the breathability additive onto the substrate.

Once the breathability additive is formed, the additive may be ground or pulverized into a powder having a desired size. For instance, in one embodiment, the breathability additive may be ground into particles having a particle size of from about 5 microns to about 50 microns. In general, the breathability additive is incorporated into an elastomeric article during formation of the article. When the elastomeric article is a glove or condom, for instance, the breathability additive may be mixed into a dispersion containing a film-forming polymer that is used in forming the article. Such an approach would be best suited for solvent-based polymer since the powder would not be soluble in the solvent and would not swell. If these particles are mixed with a water-based latex they may swell to a larger size and then shrink upon drying. The shrinkage might create voids to enhance the breathability; but, if the void were too large they could compromise the barrier properties.

Thus, in one embodiment, when the film-forming polymer is contained in an aqueous dispersion, the breathability additive may be added to the aqueous dispersion as a solution. The aqueous dispersion is then used as a dipping composition for the former during the formation of an article. Once the article is dried the polymer crosslinks and the molecular weight becomes infinite.

In an alternative embodiment, the film-forming polymer comprises a solvent-based polymer that is combined with a solvent prior to being formed into an elastomeric article. The solvent-based polymer may be, for instance, a polyurethane or a synthetic block copolymer. Examples of synthetic block copolymers that may be used in the present invention include styrene-ethylene butylene-styrene block copolymers, styrene-isoprene-styrene block copolymers, styrene-butadiene-styrene block copolymers, styrene-isoprene block copolymers, styrene-butadiene block copolymers, and mixtures thereof. Block copolymers that may be used in the present invention are disclosed, for instance, in U.S. Pat. No. 5,112,900, U.S. Pat. No. 5,407,715, U.S. Pat. No. 5,900,452, and U.S. Pat. No. 6,288,159, which are incorporated herein by reference.

The amount of breathability additive mixed with a film-forming polymer in forming a dipping composition may vary depending upon the particular application and the particular breathability additive being used. In general, the breathability additive is combined with a film-forming polymer in an amount sufficient to increase the moisture vapor transmission rate and Mocon moisture vapor transmission rate of a film formed from the resulting composition.

For example, the breathability additive may be added to a film-forming composition in an amount up to about 30% by weight, such as between about 1 and about 30 parts per hundred by weight of the film-forming polymer. In other embodiments, however, higher addition rates of the breathability additive are encompassed by the present invention. For example, in one embodiment, the breathability additive may be added to the film-forming composition in an amount up to about 30 parts per hundred by weight of the film-forming polymer. In one embodiment, the breathability additive may be added to the composition in an amount up to about 15 parts per hundred by weight of the film-forming polymer. In another embodiment, the breathability additive may be added to the composition in an amount up to about 5 parts per hundred by weight of the film-forming polymer.

The breathability additive of the present invention may generally be incorporated into any layer that is used to form an elastomeric article. For instance, in one embodiment, the breathability additive may only be incorporated into the primary layer of an elastomeric article. In other embodiments, however, the breathability additive of the present invention may be incorporated into various coatings either alone or in conjunction with being added to a primary layer. For example, if the elastomeric article is a glove or condom, the breathability additive may not only be incorporated into a primary layer, but also may be incorporated into a donning layer of the article, or a gripping layer included with the article. In one particular embodiment, for instance, the breathability additive of the present invention may be incorporated into every layer contained within the elastomeric article.

When a breathability additive is incorporated into a gripping layer or a donning layer in accordance with the present invention, in general, the gripping layer or donning layer may be made from any of the polymers described above. For instance, the gripping layer or donning layer may contain natural rubber latex, a nitrile polymer, a polyurethane polymer, an acrylic polymer, a methacrylic polymer, or mixtures thereof. In another embodiment, the donning layer or the gripping layer may be made from a synthetic block copolymer.

For example, di-block copolymers having the general formula A-B, tri-block copolymers having the general formula A-B-A', or tetrablock copolymers having the general formula A-B-A'-B', where A and A' are the same or different, and B and B' are the same or different may be used. A and A' each being a thermoplastic polymer block, for example, A and A' may be a thermoplastic polymer block that contains a styrenic moiety, and B and B' being an elastomeric polymer block such as a conjugated diene or a lower alkene polymer. In general, the elastomeric block copolymers of the present invention may contain up to about 35% styrene by weight. For example, the block copolymers may contain from about 15% to about 30% styrene. In one embodiment, block copolymers such as those available from Kraton Polymers of Houston, Tex. may be used. In these block copolymers, the polystyrene is a thermoplastic with a glass transition temperature above room temperature ($T_g$ of about 200° F.) and the elastomeric block is a rubber with a glass transition temperature well below room temperature. As such, the polystyrene and the elastomeric block are thermodynamically incompatible. Because of this incompatibility, the polystyrene blocks, being in minor proportion in the elastomeric polymer, may unite to form polystyrene domains that may be uniformly distributed throughout the elastomeric material. This creates a stable matrix similar to that of vulcanized polybutadiene, natural rubber, or styrene-butadiene rubber.

Some examples of suitable elastomeric materials include, but are not limited to, S-EB-S (styrene-ethylene butylene-styrene) block copolymers, S-I-S (styrene-isoprene-styrene) block copolymers, S-B-S (styrene-butadiene-styrene) block copolymers, S-I (styrene-isoprene) block copolymers, S-B (styrene-butadiene) block copolymers, and combinations thereof. Moreover, combinations of polymers or copolymers may be in a single layer of an article or in separate layers, such as in a multi-layer article. In a multi-layer article, one or more of the layers may include breathability additive according to the present invention.

Some block copolymers and methods for forming articles thereof are described in U.S. Pat. No. 5,112,900 to Buddenhagen, et al.; U.S. Pat. No. 5,407,715 to Buddenhagen, et al.; U.S. Pat. No. 5,900,452 to Plamthottam; and U.S. Pat. No. 6,288,159 to Plamthottam, which are incorporated herein in their entirety by reference thereto for all purposes.

When the film-forming polymer is a block copolymer as described above, the breathability additive and the polymer may be contained in a non-aqueous dipping composition. In this embodiment, for instance, a solvent may be used. The solvent can be, for instance, toluene. The breathability additive is compatible in such systems.

In another embodiment of the present invention, a coating layer containing the breathability additive of the present invention may contain a hydrophilic polymer. For example, a breathability donning layer may be formed on an elastomeric article from a solution including one or more hydrogel polymers, as are generally known in the art, and breathability additive. In certain embodiments, hydrogel polymer layers may be somewhat breathable without the addition of any breathability additive. In these particular embodiments, the process of the present invention may enhance the breathability of the layer.

Some hydrogel polymers and methods for forming hydrophilic layers thereof are described in U.S. Pat. No. 4,499,154 to James, et al.; U.S. Pat. No. 4,548,844 to Podell. et al.; and U.S. Pat. No. 3,813,695 to Podell, Jr., et al., which are incorporated herein in their entirety by reference thereto for all purposes. Exemplary hydrogel polymers include copolymers of hydroxyethylmethacrylate with methacrylic acid or with ethylhexyl acrylate or with both methacrylic acid and ethylhexyl acrylate.

Generally, a hydrogel polymer layer may be formed on an article using an aqueous solution of the hydrogel polymer. In this embodiment, the breathability additive may be simply added to the aqueous solution either before, after, or at the same time as addition of the hydrogel polymer to the water.

In one embodiment, a breathable hydrogel layer according to the present invention may include between about 4% and about 6% by weight breathability additive and between about 94% and about 96% by weight of one or more hydrogel polymers as are generally known in the art. This hydrophilic layer may be deposited on the surface of a primary or secondary layer of the substrate body and may form a donning layer on the article.

In general, the elastomeric articles including one or more breathable layers of the present invention may be formed by any suitable process. For example, article formation techniques may utilize dipping, spraying, chlorination, drying, curing, as well as any other technique known in the art.

Figure 2:
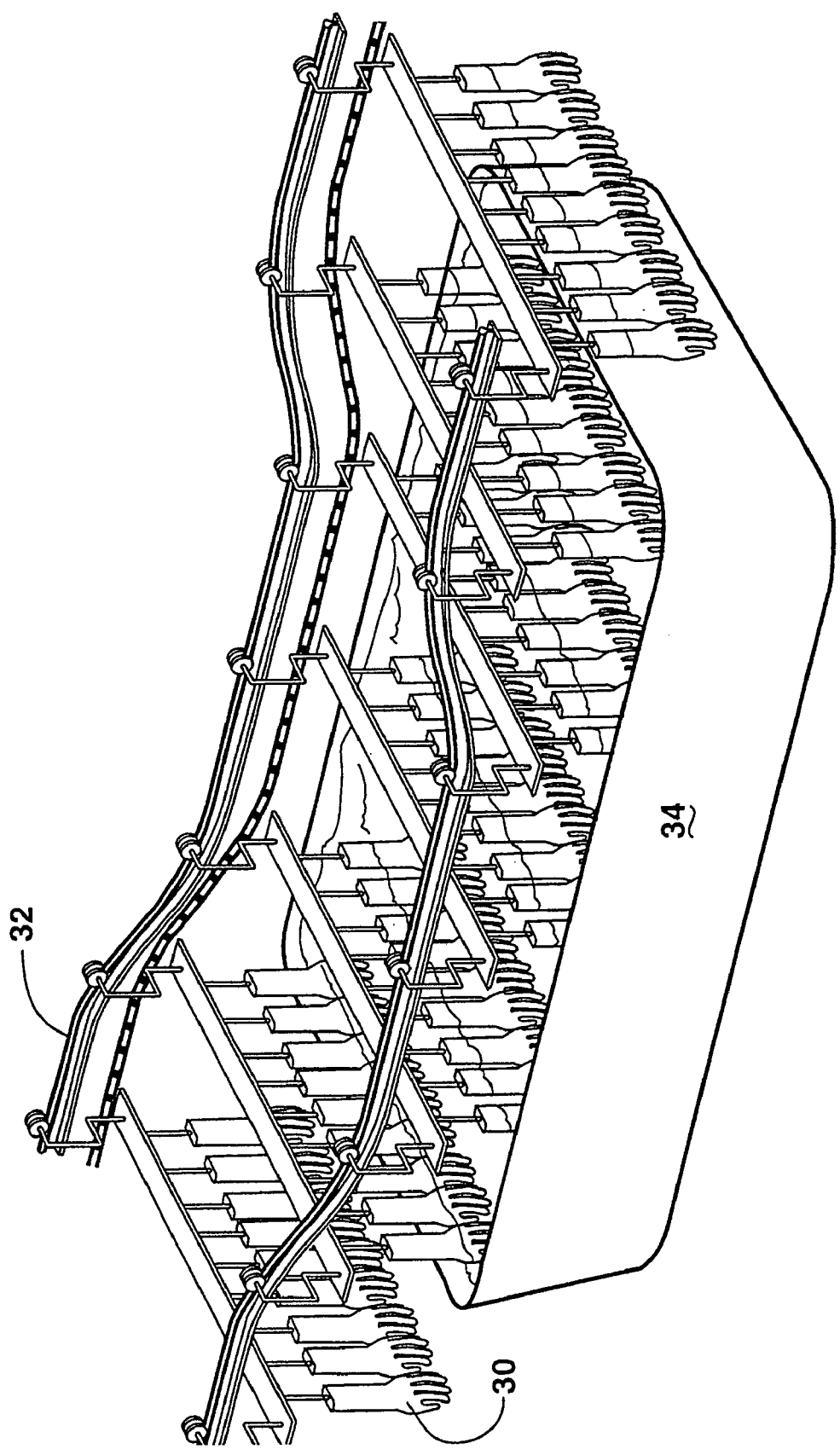
FIG. 2 is a perspective view of one embodiment of a process for dipping glove-shaped formers into a film forming composition that may be used in the process of the present invention.

In one embodiment, for instance, an article may be formed according to the present invention by a series of dipping processes of a former of the shape of the finished article. For example, FIG. 2 is an illustration of a series of glove molds or formers 30 which may be used to form the breathable elastomeric gloves of the present invention. The formers 30 shown in FIG. 2 are grouped in rows and move along a conveyor line 32. As the glove-shaped formers 30 move along the conveyor line 32, the gloves are dipped into various dipping compositions in order to form an elastomeric article. One example of a dip tank 34 is shown in the figure. As will be described in more detail below, the process may include a plurality of dip tanks containing different or the same compositions. The process line can also include various heating devices for heating films formed on the formers in order to dry the films and/or cure the films.

The process illustrated in FIG. 2 is intended to represent a continuous process. In an alternative embodiment, the glove-shaped formers 30 may be assembled into groups and process separately from other glove-shaped formers in a batch processing operation.

The formers 30 as shown in FIG. 2 are contoured molds having a textured or smooth surface which may accept a series of coatings and release the formed glove. Possible materials for the surface of the former 30 may include any suitable surface material. For example, the surface of former 30 may be formed of ceramic, porcelain, glass, metal, or certain fluorcarbons.

If desired, the formers 30 may be cleaned prior to formation of a glove on the former. The cleaning process may generally include an optional water pre-rinse followed by an acid wash. After the acid wash, the former 30 may be rinsed with water and dipped into a heated caustic solution prior to a final rinse. After the optional cleaning process, a glove may be formed on the former 30 through a series of dipping and drying steps.

When forming natural rubber latex gloves and nitrile gloves, in one embodiment, after the formers are cleaned, the formers 30 may be dipped into a coagulant composition. Depending upon the particular application, the coagulant composition may be powder-free.

In general, the coagulant composition contains a coagulant which causes a film-forming polymer such as natural rubber latex or a nitrile polymer, to coagulate and polymerize on the former thereby forming a film. Coagulants that may be used in the present invention may include a solution of a coagulant salt such as a metal salt. Examples of coagulants may include but are not limited to water-soluble salts of calcium, zinc, aluminum, and the like. For example, in one embodiment, calcium nitrate in water or alcohol may be used as the coagulant composition. The calcium nitrate, for instance, may be present in the solution in an amount up to about 40% by weight, although a greater or lesser amount may also be used. Optionally, the coagulant composition may also contain various other additives, such as surfactants.

Some coagulant compositions, however, may cause gelling of the breathability additive. In such cases, steps can be taken to prevent the breathability additive from contacting the coagulant or a coagulant may be chosen that is compatible with the breathability additive.

After being immersed in the coagulant composition, the formers 30 may be withdrawn and the coagulant present on the surface of the former may be allowed to dry. For many applications, the coagulant may air dry for a time of from about 1 minute to about 2 minutes. Once dried, a residual coating of the coagulant is left on the former.

If desired, the coagulant composition may optionally contain certain additives. For example, the coagulant composition may contain various additives, which may improve the tactile characteristics of a surface of the article. Alternatively, the coagulant composition may contain certain release aids, which facilitate later stripping of the article from the former. For example, in one embodiment, the coagulant composition can contain a powder, such as cornstarch or calcium carbonate.

After the coagulant dip, as shown in FIG. 2, the glove-shaped formers 30 may be immersed or dipped into a film-forming composition contained in a dip tank 34. The film-forming composition may be, for instance, natural rubber latex, a nitrile polymer, an acrylic polymer, a methacrylic polymer, a polyurethane, and the like. In general, when forming articles made from natural rubber latex or a nitrile polymer, the dipping composition may have a latex content of less than about 50%, although greater amounts are possible. In one embodiment, the dipping composition may be an emulsion having a latex content of less than about 25%. The dipping composition may also contain various additives such as pH adjusters, stabilizers, and the like as are generally known in the art.

Upon contact of the dipping composition with the coagulant composition, the coagulant causes the polymer contained in the dipping composition to become locally unstable and coagulate on the surface of the former. In many applications, the coagulant itself does not form a separate layer on the article, but rather becomes a part of the resulting film. Any additives in the coagulant composition may, depending upon what they are, remain between the former and the polymeric film, or alternatively may be incorporated into the polymeric film. After the desired amount of time, the glove-shaped formers 30 are withdrawn from the dipping composition, and the polymeric film left on the former is allowed to coalesce.

In some embodiments, a coagulant composition is not needed. For example, coagulant compositions may not be needed when preparing elastomeric articles from solvent-based polymers. For example, when forming an elastomeric article from a styrene-ethylene butylene-styrene block copolymer or from a styrene-isoprene-styrene block copolymer, the block copolymer may be dissolved in a solvent along with optionally a plasticizer such as a mineral oil. The solvent may be, for instance, toluene. The resulting solution is mixed using a high shear mixer and then deaerated. Next, the glove-shaped formers 30 are dipped into the composition to leave a film of the solvent-based polymer on the former.

The amount of time the former is immersed in the dipping composition determines the thickness of the film. Increasing the dwell time former in the dipping composition causes the thickness of the film to increase. Total thickness of the film forming the article body may depend upon other parameters as well, including, for example, the salt content of the dipping composition and the coagulant composition chosen.

Once the glove-shaped formers 30 are removed from the dipping composition and prior to curing the resulting film, the primary matrix of the glove now present on the former may be further processed as desired. Various pre-cure processing techniques are generally known in the art. For example, the polymeric film may be gelled with heat to strengthen the layer. If desired, the uncured layer may be leached with flowing hot water. A leaching process may extract various constituents such as salts and water, for example, from the coalesced polymer.

Prior to or after curing the primary matrix of the article, additional polymeric layers may be formed on the formers 30. This is generally done by immersing the glove-shaped formers 30 into other dipping compositions containing other film-forming polymers. The additional layers formed on the formers may comprise donning layers or gripping layers.

In some embodiments, these additional layers may be discontinuous across the surface of the article such that the breathability of the article will not be affected by the presence of the additional layer. In other embodiments, the additional layers may be continuous layers which may be breathable layers according to the present invention, i.e., through incorporation of a breathability additive, or may be otherwise breathable continuous layers. Discontinuous layers according to the present invention may be either macroscopically discontinuous, as when the material forming the layer is applied only to certain macroscopic areas of the article, or may be microscopically discontinuous, as when the material forming the layer leaves microscopic fissures or holes in the layer upon drying of the layer.

Once the body of the article is formed, such as described above, a bead roll station can, in some embodiments, be utilized to impart a cuff to the article. For instance, the bead roll station may contain one or more bead rolls such that the former is indexed therethrough to be provided with cuffs.

After one or more polymer layers are formed on the glove-shaped formers 30, the one or more polymer layers may be cured, or vulcanized if necessary. In general, the polymer may be cured by high temperature reaction with a vulcanizing agent, such as sulfur, to cause cross-linking of the polymer chains. Curing may generally take place at temperatures of about 200° F. and 300° F. In addition to curing the polymer, the high temperature process may cause the evaporation of any volatile components remaining on the former, including any water remaining in the layers.

In general, the thickness of an article formed according to the present invention may be anywhere from about 3 mil to about 15 mil. For instance, in one embodiment, the glove thickness is from about 3 mil to about 5.5 mil.

After the polymer layers are cured, if desired, the formers may be immersed into a leaching bath and leached. After drying, the formers may then be transferred to a stripping station.

The stripping station may involve automatic or manual removal of the articles from the formers. For example, in one embodiment, the articles are manually removed from each former by turning each article inside out as it is stripped from its corresponding former.

In some embodiments, after or before being stripped, the articles may be subjected to a halogenation process, such as, for example, a chlorination process, to improve the surface characteristics of the article, for example the donning slip characteristics. In one embodiment, the article may be subjected to a chlorination process following stripping and tumble-drying (which may remove any residual moisture).

For example, the article may be chlorinated through immersion and optional agitation in an aqueous solution containing dissolved chlorine. In one embodiment, several articles may be tumbled in a chlorine solution for a period of time between about 10 minutes and about 20 minutes.

After the optional halogenation process, the article may be rinsed once more in water (preferable soft water) and dried. While chlorination of the articles may decrease the breathability of the articles somewhat in certain embodiments, the articles of the present invention may still be breathable as defined in the present invention after a halogenation process.

If desired, a lubricant may also be applied to the donning surface of the elastomeric article. For example, a lubricant may be applied to the donning surface of the article using a tumbling process. In one embodiment, a lubricant layer may overlay a donning layer to aid in donning the article when the user's body is either wet, damp, or dry. The lubricant layer, for example, may include a cationic (e.g., cetyl pyridinium chloride), an anionic (e.g., sodium lauryl sulfate), or a nonionic surfactant. For instance, in one embodiment, the lubricant layer contains a quaternary ammonium compound, such as Verisoft BTMS (available from Goldschmidt Chemical Corp. of Dublin, Ohio) and a silicone emulsion (AF-60) obtained from General Electric Silicone. Verisoft BTMS contains behnyl trimethyl sulfate and cetyl alcohol, while AF-60 contains polydimethylsiloxane, acetylaldehyde, and small percentages of emulsifiers. In another embodiment, the lubricant layer 32 contains a medical-grade silicone such as Dow Corning 365 silicone, which is believed to contain water, polydimethylsiloxane, octylphenoxy polyethoxy ethanol, propylene glycol, and polyethylene glycol sorbitan monolaurate.

The features illustrated or described as part of one embodiment, may be used in another embodiment to yield a still further embodiment. Thus, it is intended that the present invention cover such modifications and variations. Having described the present invention in general terms and with reference to various embodiments, the following examples may contribute to a better understanding of the invention. Each example is provided by way of illustration and is not to be limiting of the invention.

EXAMPLES

Example 1

Two monomer solutions were prepared separately. Solution No. 1 was prepared as follows. To 14.4 grams (0.20 moles) of acrylic acid in a 200 ml beaker was added 33.3 grams of a 18% aqueous solution of polyethylene glycol 8000, followed by a solution of 3.2 grams of sodium hydroxide in 21.4 grams of distilled water. Then, 0.18 grams ($1.02 \times 10^{-3}$ moles) of ascorbic acid was added to the solution. This mixture was stirred with a magnetic stir bar at about 60 rpm in a bath of water at about 23° C. until the ascorbic acid was dissolved and the mixture cooled to 23° C.

Solution No. 2 was prepared in the following manner. To 14.4 grams (0.20 moles) of acrylic acid, in a 300 ml beaker was added to 33.3 grams of a 18% aqueous solution of polyethylene glycol 8000 (mol. wt.=8000) followed by a solution of 3.2 grams of sodium hydroxide in 21.4 grams of distilled water, 0.57 ml of 30% aqueous hydrogen peroxide and 1.0 ml ($5.42 \times 10^{-3}$ moles) of 3-(trimethoxysilyl)propyl methacrylate. The ingredients were added with stirring to produce a clear solution. This mixture was stirred with a magnetic stir bar at about 60 rpm in a bath of water at about 23° C. to provide a clear solution cooled to 23° C.

A third solution was prepared by dissolving 8 grams (0.20 moles) sodium hydroxide in 160 grams of distilled water.

Solution No. 2 was added to Solution No. 1 while stirring with a magnetic stir bar at about 60 rpm. A thermocouple was used to monitor the temperature and observe the reaction exotherm. The polymerization reaction began within about 30 seconds of mixing as the temperature rose from 23° C. to 40° C. A maximum temperature of about 70° C. was observed after three minutes of mixing the two solutions. The polymerization transformed the combined solutions into a soft gel. The gel was cut into pieces of about 1 cm$^3$ and added to the solution of 8 grams (0.20 moles) sodium hydroxide in 160 grams of distilled water. With continued stirring, aided by an Ultraturax homogenizer at 11,000 rpm, the soft gel became a viscous translucent solution.

The resulting aqueous breathability additive was cast into a film by pouring 25.1 grams of solution into a polystyrene weigh boat with surface area of about 100 cm$^2$, and allowing the water to evaporate overnight in a hood at room temperature. The resulting film weighed 4.62 grams, indicating a solution concentration of about 18.4%.

The absorbent capacity of the film was tested using the Centrifuge Retention Capacity test described in the test method section. The film had an absorbent capacity of 12.2 g/g.

Example 2

A breathability additive was synthesized, using the above mentioned method, which contained 300 grams (dry weight) of the polymer that was 79% acrylic acid (70% neutralized with sodium hydroxide) and 21% poly(ethylene glycol). The poly(ethylene glycol) had a molecular weight of about 200. Approximately one mole percent of Dow Corning Z6030 methacryl propyl trimethoxy silane was used as the latent crosslinker.

The breathability additive was then added to a standard nitrile formulation in an amount of 9.1% (on a dry weight basis). The viscosity of the blend increased significantly upon addition of the breathability additive but no appreciable latex instability, such as curds or precipitate, was observed. Some small gloves were prepared from the blend, but the high viscosity made air removal difficult. The test gloves prepared were also perceived to be higher in modulus compared to standard nitrile gloves.

Example 3

A second blend of breathability additive and nitrile was prepared in which there was 2.3% breathability additive. The breathability additive composition was prepared using the same proportions and method as those given in Example 2. The blend was stirred overnight to allow air to escape. Gloves were made according to the standard procedure for nitrile glove production. The four gloves produced had areas where remaining air was entrained.

Example 4

A third blend was prepared using 4.1% breathability additive and 95.9% nitrile formulation. The breathability additive was prepared using the same proportions as those given in Example 2. The blend was stirred over the weekend to allow air to escape. The gloves made from the blend were found to be substantially free of air entrainment.

Example 5

In this example, a blend was produced containing about 10% breathability additive and the remainder was a natural rubber formulation. The breathability additive was made in accordance with the proportions given in Example 2. Another blend which contained 5% breathability additive was also synthesized with a natural rubber latex formulation. Both of these blends were found to be incompatible with the natural rubber latex. After stirring over night at 35° C. both blends contained numerous curds of precipitated latex. As a result, gloves were not prepared from the blends with natural rubber.

The incompatibility of the breathability additive with natural rubber in this particular example is believed to be a function of the anionic charge and the density of the charge on the breathability additive polymer. Optimization of the breathability additive for use with natural rubber latex requires variation in the negative charge content by adjusting the level of acrylic acid neutralization. For instance, as stated in Example 2 above, 70 mole percent neutralized acrylic acid was used to produce the breathability additive. It is believed that by decreasing neutralization, such as less than 50 mole percent and particularly less than 30 mole percent, the breathability additive will become more compatible with natural rubber latex.

Furthermore, cationic functionality can also be incorporated into the breathability additive to improve compatibility with natural rubber latex. The incorporation of cationic functionality into the breathability additive is described in more detail above.

Test Methods

Moisture Vapor Transmission Rate Test

The following procedure is described for testing of the moisture vapor transmission rate (MVTR) for the breathable elastomeric articles of the invention. The MVTR is measured in a manner similar to ASTM Standard Test Method for Water Vapor Transmission of Materials, Designation E-96-80. A few 3-inch diameter (76 mm) circular samples are cut from the test material and from a control material, CELGUARD® 2500 (Hoechst Celanese Corporation). CELGUARD® 2500 is a 0.0025 cm thick film composed of microporous polypropylene. Two or three samples are prepared for each material.

The cups used for testing are cast aluminum, flanged, 2 inches deep and come with a mechanical seal and neoprene gasket. The cups are distributed by Thwing-Albert Instrument Company, Philadelphia, Pa., under the designation Vapometer cup #681. One hundred millimeters of distilled water is poured into each Vapometer cup, and each of the individual samples of the test materials and control material are placed across the top area of an individual cup. Screw-on flanges are tightened to form a seal along the edges of the cups leaving the associated test material or control material exposed to the ambient atmosphere over a 62-millimeter diameter circular area (an open, exposed area of about 30 cm$^2$). The cups are then weighed, placed on a tray, and set in a forced air oven set at 100° F. (38° C.).

A constant temperature oven with external air through it is used to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary test MVTR value is calculated as follows:

Test MVTR=[(grams weight loss over 24 hours)×7571]÷24

The relative humidity within the oven is not specifically controlled. Under predetermined set conditions of 100° F. and ambient relative humidity, the MVTR for CELGUARD® 2500 has been determined to be 5000 g/m²/24 hours. Accordingly, CELGUARD® 2500 is run as a control sample with each test and the resulting values are corrected in accord with the variation of the control relative to its known MVTR.

Mocon Water Vapor Transmission Rate Test

A suitable technique for determining the WVTR (water vapor transmission rate) value of a material is the test procedure standardized by INDA (Association of the Nonwoven Fabrics Industry), number IST-70.4-99, entitled "STANDARD TEST METHOD FOR WATER VAPOR TRANSMISSION RATE THROUGH NONWOVEN AND PLASTIC FILM USING A GUARD FILM AND VAPOR PRESSURE SENSOR" which is incorporated by reference herein. The INDA procedure provides for the determination of WVTR, the permeance of the film to water vapor and, for homogeneous materials, water vapor permeability coefficient.

The INDA test method is well known and will not be set forth in detail herein. However, the test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W model 100K manufactured by Mocon/Modern Controls, Inc, Minneapolis, Minn. A first test is made of the WVTR of the guard film and air gap between an evaporator assembly that generates 100 percent relative humidity. Water vapor diffuses through the air gap and the guard film and then mixes with a dry gas flow which is proportional to water vapor concentration. The electrical signal is routed to a computer for processing. The computer calculates the transmission rate of the air gap and guard film and stores the value for further use.

The transmission rate of the guard film and air gap is stored in the computer as CalC. The sample material is then sealed in the test cell. Again, water vapor diffuses through the air gap to the guard film and the test material and then mixes with a dry gas flow that sweeps the test material. Also, again, this mixture is carried to the vapor sensor. The computer then calculates the transmission rate of the combination of the air gap, the guard film, and the test material. This information is then used to calculate the transmission rate at which moisture is transmitted through the test material according to the equation:

$TR^{-1}_{test\ material} = TR^{-1}_{test\ material,\ guardfilm,\ airgap} - TR^{-1}_{guardfilm,\ airgap}$ Calculations:
WVTR: The calculation of the WVTR uses the formula:

$$WVTR = \frac{F\rho_{sat}(T)RH}{A\rho_{sat}(T)(1-RH)}$$

where:
F=The flow of water vapor in cc/min.,
$\rho_{sat}$ (T)=The density of water in saturated air at temperature T,
RH=The relative humidity at specified locations in the cell, A
A=The cross sectional area of the cell, and,
$p_{sat}$(T)=The saturation vapor pressure of water vapor at temperature T Test Results The gloves prepared in Examples 3 and 4 above were tested for water vapor transmission rate. Nitrile gloves not containing the breathability additive were also tested for comparative reasons.

As shown below, addition of the breathability additive into the nitrile formulation significantly increased the WVTR values.

| % Breathability Additive Contained in Nitrile Formulation: | Control 0% | Example No. 3 2.3% | Example No. 4 4.1% |
|---|---|---|---|
| WVTR Results: (Units: g/m²/24 hours) | 165.187 | 208.821 | 233.755 |
| | 165.187 | 218.171 | 261.805 |
| | 177.654 | 218.171 | 239.988 |
| | 174.537 | 224.404 | 224.404 |
| | | 208.821 | 224.404 |
| | | 202.587 | 227.521 |
| | | 258.688 | |
| | | 252.455 | |
| Average: | 170.641 | 224.015 | 235.313 |

Although various constructions and techniques for forming elastomeric gloves have been described above, it should be understood that the present invention is not limited to any particular construction or technique for forming the glove. For example, the layers described above may not be utilized in all instances. Additionally, other layers not specifically referred to above may be utilized in the present invention.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:
1. An elastomeric article comprising:
a substrate body comprising at least one layer of a material, the at least one layer being made from a film-forming polymer, the substrate body having an inside surface and an outside surface; and
a breathability additive incorporated into the at least one layer of the substrate body, the breathability additive comprising an acrylic acid or salt, a polyolefin glycol or oxide, and a latent crosslinking agent.

2. An elastomeric article as defined in claim 1, wherein the at least one layer comprises a material selected from the group consisting of natural rubber latex, a nitrile polymer, a polyurethane polymer, a polyvinyl chloride polymer, a silicone polymer, a styrene-ethylene butylene-styrene block copolymer, or a styrene-isoprene-styrene block copolymer.

3. An elastomeric article as defined in claim 1, wherein the at least one layer comprises a nitrile polymer.

4. An elastomeric article as defined in claim 1, wherein the breathability additive is present in the at least one layer in an amount sufficient to increase the moisture vapor transmission rate of the elastomeric article.

5. An elastomeric article as defined in claim 1, wherein the breathability additive is present in the at least one layer in an amount sufficient to increase the Mocon moisture vapor transmission rate of the elastomeric article.

6. An elastomeric article as defined in claim 1, wherein the at least one layer is a primary elastic layer of the elastomeric article.

7. An elastomeric article as defined in claim 1, wherein the breathability additive is present in the at least one layer in an amount of from about 1 mass percent to about 30 mass percent.

8. An elastomeric article as defined in claim 1, wherein the elastomeric article further comprises a donning layer in addition to the at least one layer.

9. An elastomeric article as defined in claim 1, wherein the elastomeric article is a glove.

10. An elastomeric article as defined in claim 1, wherein the elastomeric article is a condom.

11. An elastomeric article comprising:
a substrate body comprising at least one layer of a material, the at least one layer being made from a film-forming polymer, the substrate body having an inside surface and an outside surface; and
a breathability additive incorporated into the at least one layer of the substrate body, the breathability additive comprising about 15 to about 99.9% by mass monoethylenically unsaturated polymer units, about 0.1 to about 20% by mass ester units selected from the group consisting of acrylate and methacrylate ester units that include an alkoxysilane functionality, and about 0.1 to about 75% by mass of units selected from the group consisting of polyolefin glycol and polyolefin oxide units.

12. An elastomeric article as defined in claim 11, wherein the breathability additive is present in the at least one layer in an amount sufficient to increase the moisture vapor transmission rate of the elastomeric article.

13. An elastomeric article as defined in claim 11, wherein the breathability additive is present in the at least one layer in an amount sufficient to increase the Mocon moisture vapor transmission rate of the elastomeric article.

14. An elastomeric article as defined in claim 11, wherein the at least one layer comprises natural rubber latex.

15. An elastomeric article as defined in claim 11, wherein the at least one layer comprises a nitrile polymer.

16. An elastomeric article as defined in claim 11, wherein the at least one layer is a primary elastic layer of the article.

17. An elastomeric article as defined in claim 11, wherein the at least one layer comprises a block copolymer.

18. An elastomeric article as defined in claim 11, wherein the at least one layer comprises a donning layer.

19. An elastomeric article as defined in claim 11, wherein the at least one layer comprises a grip layer.

20. An elastomeric article as defined in claim 11, wherein the breathability additive is incorporated into the at least one layer in an amount from about 1 to about 30 parts per hundred by weight of the film-forming polymer.

21. An elastomeric article as defined in claim 11, wherein the breathability additive is incorporated into the at least one layer in an amount up to about 30 mass percent of the layer.

22. An elastomeric article as defined in claim 11, wherein the breathability additive is present in every layer of the substrate body.

23. An elastomeric article as defined in claim 11, wherein the elastomeric article is a glove.

24. An elastomeric article as defined in claim 11, wherein the elastomeric article is a condom.

25. A process for forming an elastomeric article comprising:
providing dip composition containing a film-forming polymer and a breathability additive, the breathability additive comprising about 15 to about 99.9% by mass monoethylenically unsaturated polymer units, about 0.1 to about 20% by mass ester units elected from the group consisting of acrylate and methacrylate ester units that include an alkoxysilane functionality, and about 0.1 to about 75% by mass of units selected from the group consisting of polyolefin glycol and polyolefin oxide units;
dipping a former into the composition and withdrawing the former from the composition so as to form a film on the former, the film containing the polymer and the breathability additive;
drying the film on the former; and
stripping the film from the former to form an elastomeric article.

26. A process as defined in claim 25, wherein the polymer comprises a natural rubber latex.

27. A process as defined in claim 25, wherein the polymer comprises a nitrile polymer.

28. A process as defined in claim 25, wherein the polymer comprises a block copolymer.

29. A process as defined in claim 25, wherein the breathability additive is added to the composition as a solution.

30. A process as defined in claim 25, wherein the breathability additive is present in the composition in an amount up to about 30 mass percent.

31. A process as defined in claim 25, wherein the breathability additive is present in the composition in an amount of from about 0.5 mass percent to about 10 mass percent.

32. A process as defined in claim 25, further comprising the step of curing the polymer contained in the film.

33. A process as defined in claim 25, further comprising the step of forming a donning layer on the elastomeric article.

34. A process as defined in claim 25, further comprising the step of chlorinating at least one surface of the elastomeric article.

35. A process as defined in claim 25, wherein the elastomeric article is a glove.

36. A process as defined in claim 25, wherein the elastomeric article is a condom.

* * * * *